(12) United States Patent
Schlotterback et al.

(10) Patent No.: US 11,555,642 B2
(45) Date of Patent: Jan. 17, 2023

(54) COLD THERAPY COOLER APPARATUS

(71) Applicants: Ryan Schlotterback, Fort Wayne, IN (US); Richard Potts, Winona Lake, IN (US)

(72) Inventors: Ryan Schlotterback, Fort Wayne, IN (US); Richard Potts, Winona Lake, IN (US)

( * ) Notice: Subject to any disclaimer, the term of this patent is extended or adjusted under 35 U.S.C. 154(b) by 133 days.

(21) Appl. No.: 17/322,996

(22) Filed: May 18, 2021

(65) Prior Publication Data

US 2021/0364218 A1 Nov. 25, 2021
US 2022/0341646 A2 Oct. 27, 2022

Related U.S. Application Data

(60) Provisional application No. 63/028,052, filed on May 21, 2020.

(51) Int. Cl.
*F25D 17/02* (2006.01)
*A61F 7/00* (2006.01)
*F25D 3/00* (2006.01)

(52) U.S. Cl.
CPC ............ *F25D 17/02* (2013.01); *A61F 7/0085* (2013.01); *F25D 3/00* (2013.01); *A61F 2007/0056* (2013.01)

(58) Field of Classification Search
CPC .... F25D 3/00; F25D 17/02; A61F 2007/0056; A61F 7/0085; F16L 5/14; H02G 3/22
See application file for complete search history.

(56) References Cited

U.S. PATENT DOCUMENTS

| | | | |
|---|---|---|---|
| 6,551,348 B1* | 4/2003 | Blalock ................. | A61F 7/0085 607/104 |
| 2008/0060374 A1* | 3/2008 | Gammons ................. | F25D 3/08 607/104 |
| 2010/0030306 A1* | 2/2010 | Edelman ................... | A61F 7/02 607/104 |
| 2011/0042935 A1* | 2/2011 | Bain ........................ | F16L 5/14 285/31 |

* cited by examiner

*Primary Examiner* — Cassey D Bauer

(57) ABSTRACT

A Cold Therapy Cooler Apparatus includes a port body with a flange and threads that is inserted into an orifice in the sidewall or lid of a cooler. An interior retaining ring with compatible threads cooperates with the flange to retain the port body within the orifice. A circulating pump is inside the cooler. An internal supply hose is connected to the pump, and to a supply pass-through that passes through the port body and is connected to an exterior supply hose. An internal return hose is connected to the pump, and to a return pass-through that passes through the port body and is connected to an exterior return hose. The exterior hoses are connected to an anatomical area cooling device. A power cord is connected to the pump and to a power cord connection by way of a power cord pass-through that passes through the port body.

20 Claims, 5 Drawing Sheets

COLD THERAPY COOLER APPARATUS

CROSS-REFERENCE TO RELATED APPLICATIONS

The present application claims benefit under 35 U.S.C. § 119(e) of U.S. Provisional Application No. 63/028,052, filed May 21, 2020, the disclosure of which is expressly incorporated by reference herein in its entirety.

BACKGROUND

Field of Invention

Embodiments of the present invention described herein generally relate to a Cold Therapy Cooler Apparatus. The Cold Therapy Cooler Apparatus is designed as part of a cold therapy system. The Cold Therapy Cooler Apparatus allows for the cooler part of the cold therapy system to be converted into a recreational or other use cooler when it is no longer being used as a cooler for the purpose of cold therapy.

Related Art

Cold therapy systems often include a cooler that is used to provide cold water, such as from a mixture of ice and water, which is circulated using a pump, hoses, and a bladder or other anatomical area cooling device. The bladder or other anatomical area cooling device acts as a heat exchanger at the target body site, in order to cool that anatomical area for the purposes of pain relief and rehabilitation. The coolers of known cold therapy systems are single purpose dedicated coolers, so that when not in use for cold therapy, the cooler cannot readily be used for any other purpose. Moreover, medical conditions requiring the use of cold therapy systems are commonly short term conditions, such as post-injury treatments or treatments following surgical intervention.

As a result, cold therapy systems may only be used for four to six weeks for a given treatment. This often leaves the consumer with an expensive cold therapy system that then gets discarded or put into storage in case it is needed again, if at all. Due to their single purpose dedicated configuration, neither the cooler of known cold therapy systems nor any of the other components thereof are able to be conveniently repurposed. Accordingly, there is an unmet need for a cold therapy system that includes a cooler that may conveniently be repurposed so that it does not get discarded or take up space in storage unnecessarily.

SUMMARY

Embodiments described herein relate to a Cold Therapy Cooler Apparatus. The Cold Therapy Cooler Apparatus is designed so that the cooler thereof may be readily repurposed for recreational use via intentionally designed modularity. However, this recited purpose is exemplary, and is not to be considered limiting in any way, as embodiments of the Cold Therapy Cooler Apparatus may be used for medical, research, industrial, or commercial purposes wherein interchangeability of function of the cooler element is desired.

Specifically, the cooler used as part of the Cold Therapy Cooler Apparatus is provided with a pump for circulating cooling fluid, for non-limiting example water. Preferably, this pump may be a small, low voltage immersion pump that is positioned within the cooler at the bottom. Low voltage for the purposes of this disclosure means preferably between 6 and 50 volts DC, more preferably between 12 and 24 volts DC. By way of its placement within the cooler at the bottom thereof, the pump is self-priming, is protected from external damage, and is not easily separated from the system or lost.

In order to provide power to the pump, and in order to provide a supply and return line to the hoses and bladder or other anatomical area cooling device, a cold therapy port has a cold therapy port body with a power cord pass-through, a supply hose pass-through, and a return hose pass-through. The power cord pass-through, the supply hose pass-through, and the return hose pass-through may have a power cord connection, a supply hose connection, and a return hose connection, respectively, arranged in an exterior recess of the cold therapy port body, in order to further protect the power cord connection, the supply hose connection, and the return hose connection from damage. The cold therapy port is arranged in a single orifice that may be positioned in the side or end of the cooler, or in the lid thereof.

The orifice is specifically designed for the cold therapy port and its pass-through components to allow the cooler to be used for cold therapy. However, when not in use as a cold therapy apparatus, the cold therapy port may easily be replaced with additional modular variations or options. These may include an insulated solid port body, a port having a drain, a port having a vent (for non-limiting example for use with dry ice), a port having a liquid dispenser, and other variations. The modular interchangeability between the cold therapy port and the insulated solid port body, or other port variations, allows a consumer to get additional use from the cooler of the cold therapy system, as it allows conversion of the cold therapy cooler to a usable recreation or other use cooler. The insulated solid port body may incorporate an insulation component to provide thermal insulation similar to that of a cooler not having any port at all. The ability of the user to simply remove the cold therapy port and internal components provides an easy conversion and allows the user to get additional functionality from the Cold Therapy Cooler Apparatus. The Cold Therapy Cooler Apparatus may be embodied as any of a number of different cooler styles, including for non-limiting example rolling coolers, soft sided coolers, and etcetera.

According to one embodiment of the Cold Therapy Cooler Apparatus, a cooler has a single orifice located in its sidewall or lid. A cold therapy port body is inserted into the single orifice, The cold therapy port body has a port body flange and a first engagement feature. A circulating pump is positioned within the cooler. An internal supply hose is connected to the circulating pump, and to a supply hose pass-through that passes through the cold therapy port body by way of a supply hose hole. The supply hose pass-through is connected to an exterior supply hose by way of a supply hose connection. An internal return hose is connected to a return hose pass-through that passes through the cold therapy port body by way of a return hose hole. The return hose pass-through is connected to an exterior return hose by way of a return hose connection. The exterior supply hose and the exterior return hose are connected to a bladder or other anatomical area cooling device.

According to one embodiment of the Cold Therapy Cooler Apparatus, a method of providing Cold Therapy includes several steps. The first step is providing a cooler having a single orifice, The second step is providing a cold therapy port body having a port body flange and a first engagement feature. The third step is inserting the cold therapy port body into the single orifice. The fourth step is positioning a circulating pump within the cooler. The fifth step is connecting an internal supply hose to the circulating pump, and to a supply hose pass-through that passes through the cold therapy port body by way of a supply hose hole. The sixth step is connecting the supply hose pass-through to an exterior supply hose by way of a supply hose connection. The seventh step is connecting an internal return hose to a return hose pass-through that passes through the cold therapy port body by way of a return hose hole. The eighth step is connecting the return hose pass-through to an exterior return hose by way of a return hose connection. The ninth step is connecting the exterior supply hose and the exterior return hose to a bladder or other anatomical area cooling device.

DESCRIPTION OF THE DRAWINGS

The above-mentioned and other features of embodiments of the Cold Therapy Cooler Apparatus, and the manner of their working, will become more apparent and will be better understood by reference to the following description of embodiments of the Cold Therapy Cooler Apparatus taken in conjunction with the accompanying drawings, wherein.

Corresponding reference numbers indicate corresponding parts throughout the several views. The exemplifications set out herein illustrate embodiments of the Cold Therapy Cooler Apparatus, and such exemplifications are not to be construed as limiting the scope of the claims in any manner.

DETAILED DESCRIPTION

The following detailed description and appended drawing describe and illustrate various exemplary embodiments of the invention. The description and drawings serve to enable one skilled in the art to make and use the invention, and are not intended to limit the scope of the invention in any manner. In respect of any methods disclosed and illustrated, the steps presented are exemplary in nature, and thus, the order of the steps is not necessary or critical.

Figure 1:
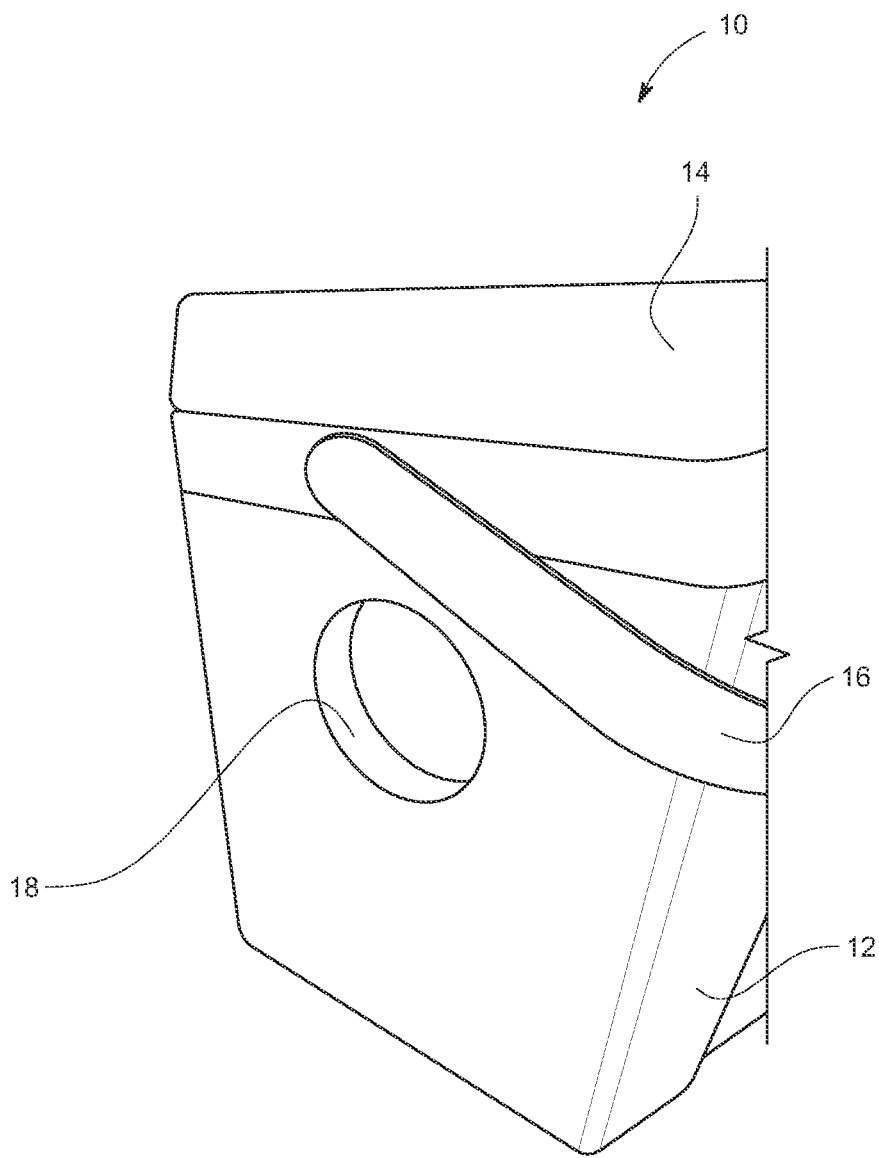
FIG. 1 is a partial perspective view of a cooler being prepared for conversion to an embodiment of the Cold Therapy Cooler Apparatus of the present invention, as described herein.
Figure 2:
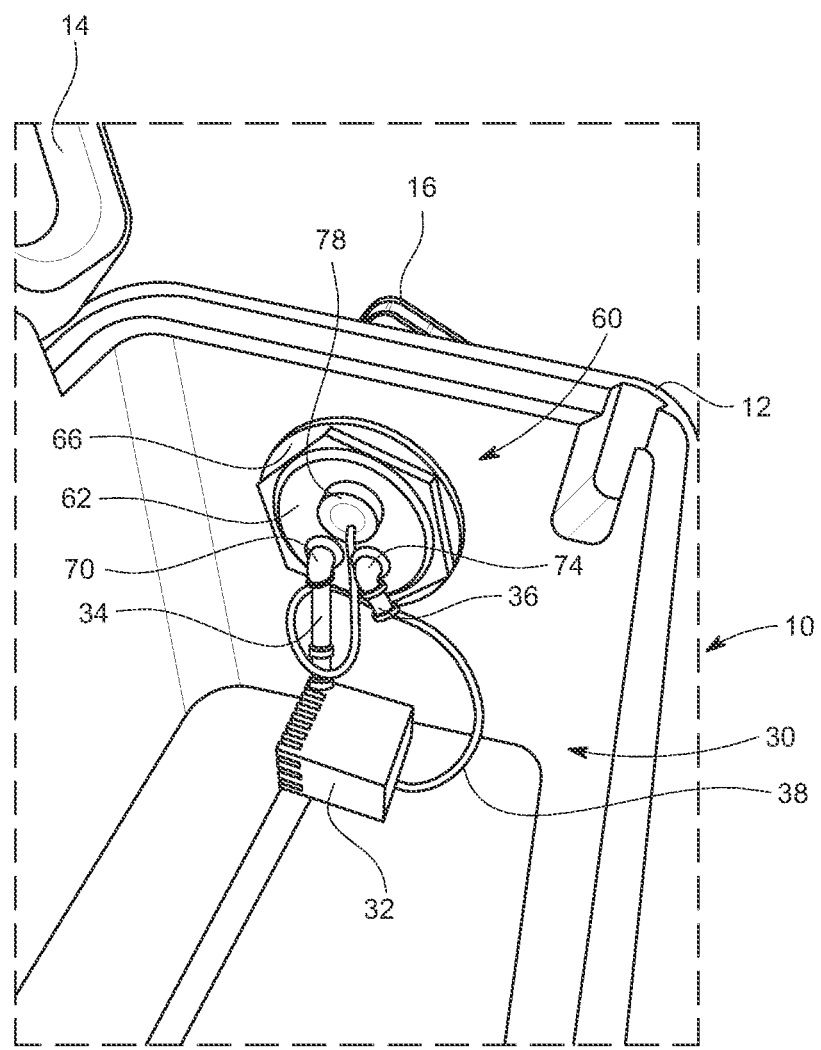
FIG. 2 is a partial perspective interior view of an embodiment of the Cold Therapy Cooler Apparatus of the present invention, as described herein.
Figure 3:
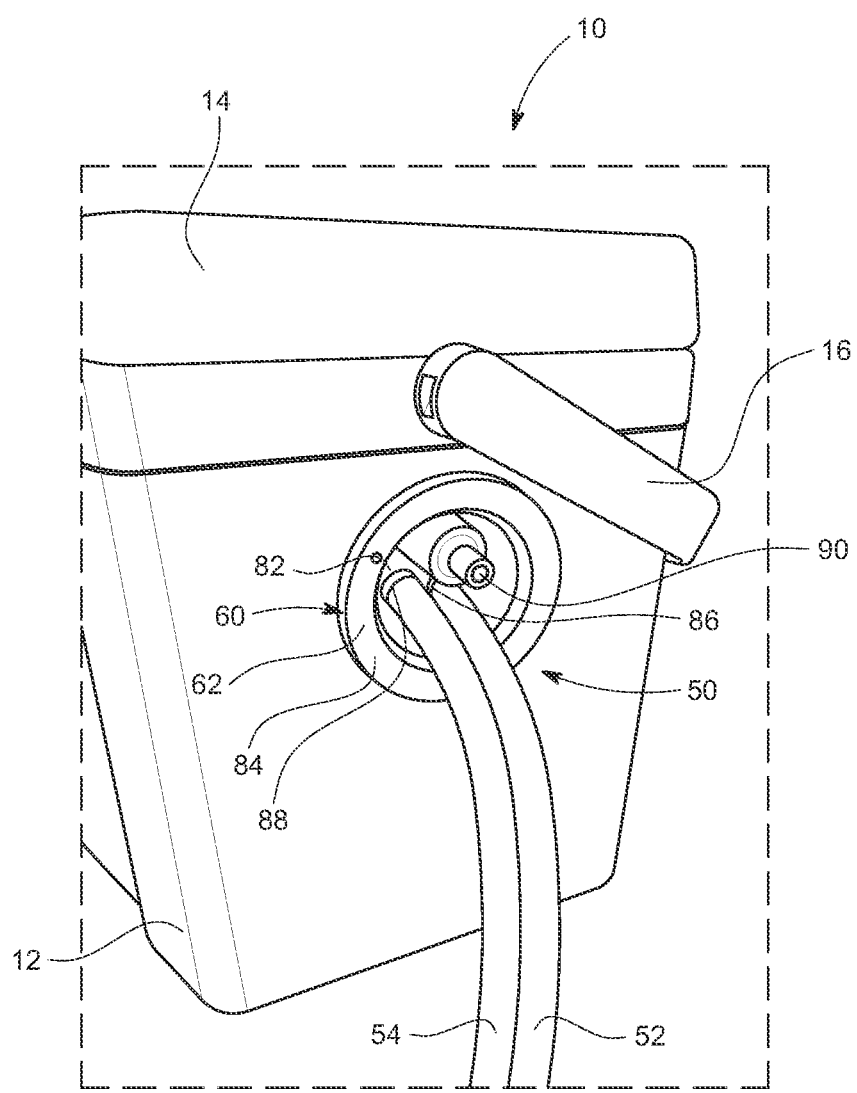
FIG. 3 is a partial perspective exterior view of an embodiment of the Cold Therapy Cooler Apparatus of the present invention, as described herein.

Turning now to FIGS. 1 through 3, a non-limiting exemplary embodiment of the Cold Therapy Cooler Apparatus 10 is shown. A cooler 12 is provided with a cooler lid 14 and a cooler handle 16. A single orifice 18 is provided in one of the sidewalk of the cooler 12, into which a cold therapy port 60 is inserted. Alternately, the single orifice 18 may be provided in the cooler lid 14 of the cooler 12. The cold therapy port 60 is formed of a cold therapy port body 62 having an exterior recess 82 and a port body flange 84. An interior retaining ring 66 may be engaged with the cold therapy port body 62 in the interior of the cooler 12. Engagement between the cold therapy port body 62 and the interior retaining ring 66 may be by way of threads, a twist lock feature, or snap-in features. The interior retaining ring 66 and the port body flange 84 cooperate to hold the cold therapy port body 62 of the cold therapy port 60 in place. Alternately, the cold therapy port body 62 may directly engage with the single orifice 18 by way of threads, twist lock feature, snap-in features, or other engagement features.

A supply hose pass-through 70 passes through the cold therapy port body 62 and connects with an internal supply hose 34 within the cooler 12, and connects with an exterior supply hose 52 by way of a supply hose connection 86 outside of the cooler 12, Similarly, a return hose pass-through 74 passes through the cold therapy port body 62 and connects with an internal return hose 36 within the cooler 12, and connects with an exterior return hose 54 by way of a return hose connection 88 outside of the cooler 12. The internal components 30 of the Cold Therapy Cooler Apparatus 10, then, include the internal supply hose 34, the internal return hose 36, and a circulating pump 32.

The circulating pump 32 pumps cooling fluid out of the cooler 12 by way of the internal supply hose 34, the supply hose pass-through 70, the supply hose connection 86, and the exterior supply hose 52. The cooling fluid circulates through a bladder or other anatomical area cooling device (not shown) for the purpose of providing cooling to an anatomical area, before returning to the cooler 12 by way of the exterior return hose 54, the return hose connection 88, the return hose pass-through 74, and the internal return hose 36. The exterior components 50, then, include the supply hose connection 86, the exterior supply hose 52, the bladder or other anatomical area cooling device (not shown), the exterior return hose 54, and the return hose connection 88. A power cord connection 90 may provide low voltage electrical power from a transformer or from a battery pack to the circulating pump 32 by way of a power cord 38 that passes through the cold therapy port body 62 by way of a power cord pass-through 78. Alternately, the circulating pump 32 may be self-powered, such as by way of an internal battery.

Figure 4:
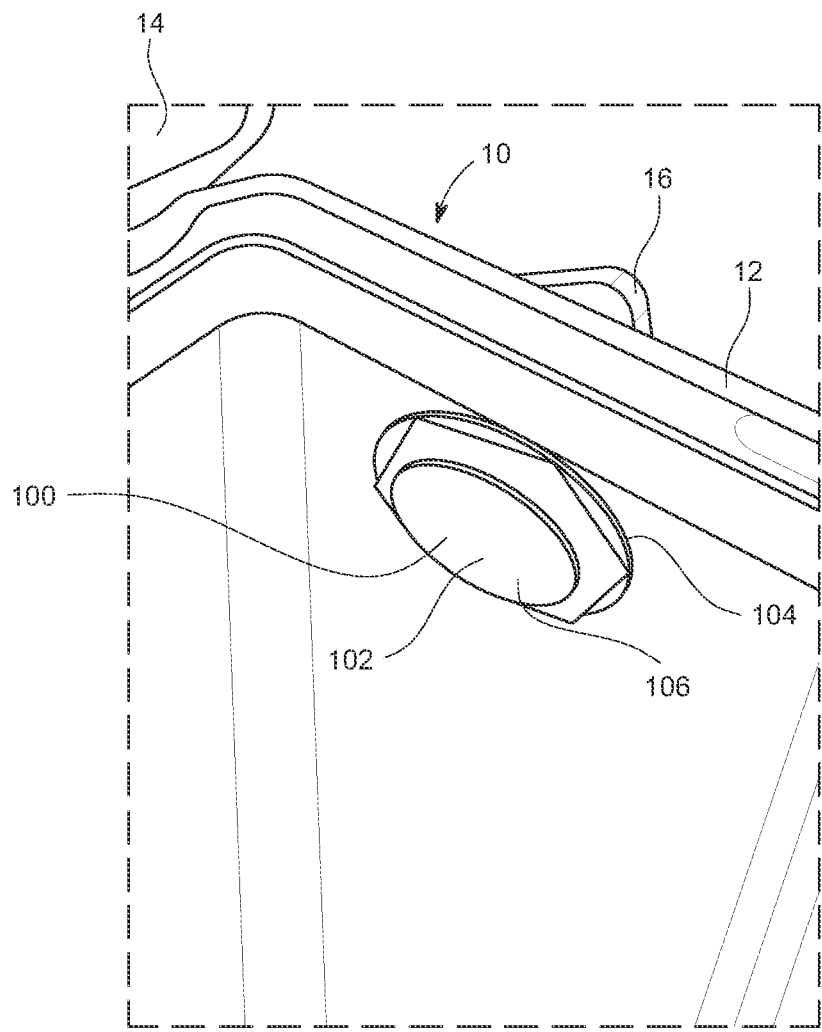
FIG. 4 is a partial perspective interior view of an embodiment of the Cold Therapy Cooler Apparatus of the present invention, as described herein.

Turning now to FIG. 4, an embodiment of the Cold Therapy Cooler Apparatus 10 again includes a cooler 12 having a cooler lid 14 and a cooler handle 16. The cold therapy port 60 (not shown) within the single orifice 18 (not visible) has now been replaced with a solid port 100 having a solid port body 102. The solid port body 102 has a port body flange (not shown) that cooperates with an interior retaining ring 104 to hold the solid port body 102 in place. Alternately, the solid port body 102 may directly engage with the single orifice 18 by way of threads or other engagement features. The solid port 100 may be provided with an insulation component 106 to provide insulation similar to that of a cooler not having any port at all.

Figure 5A:
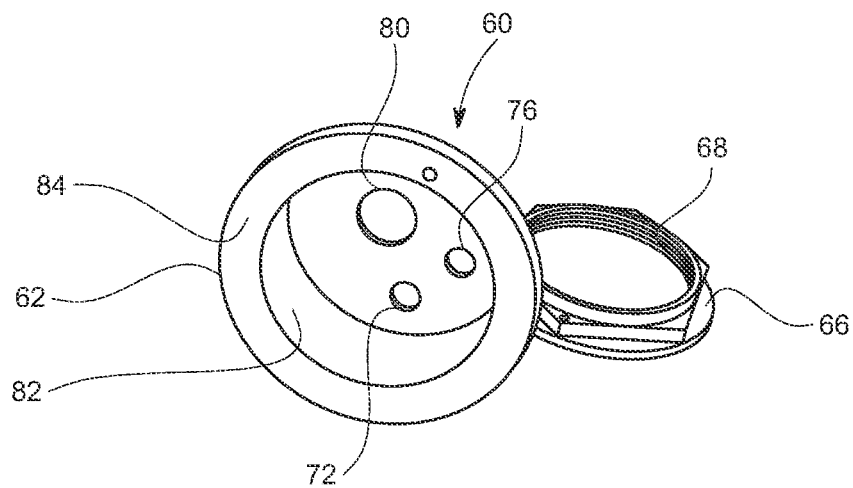
FIG. 5A is a perspective view of components of an embodiment of the Cold Therapy Cooler Apparatus of the present invention, as described herein.
Figure 5B:
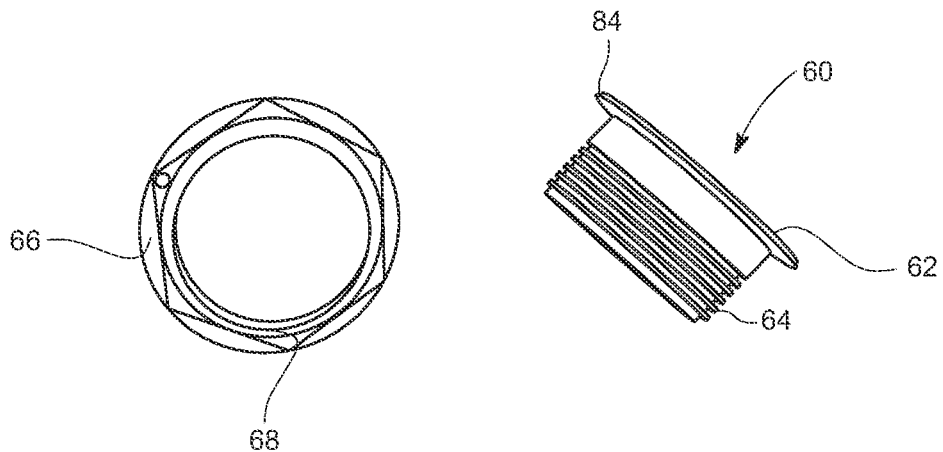
FIG. 5B is a perspective view of components of an embodiment of the Cold Therapy Cooler Apparatus of the present invention, as described herein.

FIGS. 5A and 5B show the cold therapy port 60 again being formed of a cold therapy port body 62 having an exterior recess 82 and a port body flange 84, An interior retaining ring 66 is engageable with the cold therapy port body 62 by way of engagement feature 68 that connects to an engagement feature 64 on the cold therapy port body 62. The interior retaining ring 66 and the port body flange 84 cooperate to hold the cold therapy port body 62 of the cold therapy port 60 in place in the wall of the cooler 12 (not shown). A supply hose hole 72 is provided for the supply hose pass-through 70 (not shown). A return hose hole 76 is provided for the return hose pass-through 74 (not shown). Finally, a power cord hole 80 is provided for the power cord pass-through 78 (not shown).

While the Cold Therapy Cooler Apparatus has been described with respect to at least one embodiment, the Cold Therapy Cooler Apparatus can be further modified within the spirit and scope of this disclosure, as demonstrated previously. This application is therefore intended to cover any variations, uses, or adaptations of the Cold Therapy Cooler Apparatus using its general principles. Further, this application is intended to cover such departures from the present disclosure as come within known or customary practice in the art to which the disclosure pertains and which fall within the limits of the appended claims.

REFERENCE NUMBER LISTING

10 Cold Therapy Cooler Apparatus
12 Cooler
14 Cooler lid
16 Cooler handle
18 Single orifice
30 Internal components
32 Circulating pump
34 Internal supply hose
36 Internal return hose
38 Power cord
50 Exterior components
52 Exterior supply hose
54 Exterior return hose
60 Cold therapy port
62 Cold therapy port body
64 Engagement feature
66 Interior retaining ring
68 Engagement feature
70 Supply hose pass-through
72 Supply hose hole
74 Return hose pass-through
76 Return hose hole
78 Power cord pass-through
80 Power cord hole
82 Exterior recess
84 Port body flange
86 Supply hose connection
88 Return hose connection
90 Power cord connection
100 Solid port
102 Solid port body
104 Interior retaining ring
106 Insulation component

What is claimed is:

1. A Cold Therapy Cooler Apparatus, comprising:
a cooler having a single orifice;
a cold therapy port body having a port body flange and a first engagement feature, the cold therapy port body being inserted into the single orifice;
a circulating pump positioned within the cooler;
an internal supply hose connected to the circulating pump, and to a supply hose pass-through that passes through the cold therapy port body by way of a supply hose hole, the supply hose pass-through being connected to an exterior supply hose by way of a supply hose connection;
an internal return hose connected to a return hose pass-through that passes through the cold therapy port body by way of a return hose hole, the return hose pass-through being connected to an exterior return hose by way of a return hose connection; and
the exterior supply hose and the exterior return hose being connected to a bladder or other anatomical area cooling device.

2. The Cold Therapy Cooler Apparatus of claim 1, wherein:
the single orifice being arranged in one of a sidewall of the cooler and a lid of the cooler.

3. The Cold Therapy Cooler Apparatus of claim 1, further comprising:
an interior retaining ring having a second engagement feature engageable with the first engagement feature, the interior retaining ring and the port body flange cooperating to retain the cold therapy port body within the single orifice.

4. The Cold Therapy Cooler Apparatus of claim 3, wherein:
first and second engagement features being one of threads, twist lock features, and snap-in features.

5. The Cold Therapy Cooler Apparatus of claim 3, further comprising:
a power cord connected to the circulating pump and to a power cord connection by way of a power cord pass-through, the power cord pass-through passing through the cold therapy port body by way of a power cord hole.

6. The Cold Therapy Cooler Apparatus of claim 5, wherein:
the cold therapy port body having an exterior recess, the supply hose connection, the return hose connection, and the power cord connection being arranged within the exterior recess of the cold therapy port body.

7. The Cold Therapy Cooler Apparatus of claim 3, further comprising:
an interchangeable port body, the interchangeable port body being one of an insulated solid port body, a port having a drain, a port having a vent, and a port having a liquid dispenser;
the interchangeable port body being interchangeable with the cold therapy port body and retainably engageable with the single orifice.

8. The Cold Therapy Cooler Apparatus of claim 7, wherein:
the insulated solid port body incorporating an insulation component configured to provide thermal insulation.

9. The Cold Therapy Cooler Apparatus of claim 1, wherein:
the circulating pump being a low voltage immersion pump.

10. The Cold Therapy Cooler Apparatus of claim 9, wherein:
the low voltage immersion pump being at least one of:
configured to operate on between 12 and 24 volts DC, and
self-priming.

11. The Cold Therapy Cooler Apparatus of claim 1, wherein:
the cooler being embodied as one of a portable ice chest, a rolling cooler, and a soft sided cooler.

12. A method of providing Cold Therapy, comprising the steps of:
providing a cooler having a single orifice;
providing a cold therapy port body having a port body flange and a first engagement feature;
inserting the cold therapy port body into the single orifice;
positioning a circulating pump within the cooler;

connecting an internal supply hose to the circulating pump, and to a supply hose pass-through that passes through the cold therapy port body by way of a supply hose hole;

connecting the supply hose pass-through to an exterior supply hose by way of a supply hose connection;

connecting an internal return hose to a return hose pass-through that passes through the cold therapy port body by way of a return hose hole;

connecting the return hose pass-through to an exterior return hose by way of a return hose connection; and connecting the exterior supply hose and the exterior return hose to a bladder or other anatomical area cooling device.

13. The method of claim 12, further comprising the step of:

arranging the single orifice in one of a sidewall of the cooler and a lid of the cooler.

14. The method of claim 12, further comprising the steps of:

providing an interior retaining ring having a second engagement feature engageable with the first engagement feature; and retaining the cold therapy port body within the single orifice using the interior retaining ring and the port body flange.

15. The method of claim 14, wherein:

first and second engagement features being one of threads, twist lock features, and snap-in features.

16. The method of claim 14, further comprising the steps of:

connecting a power cord to the circulating pump and to a power cord connection by way of a power cord pass-through; and passing the power cord pass-through through the cold therapy port body by way of a power cord hole.

17. The method of claim 16, further comprising the steps of:

providing the cold therapy port body with an exterior recess; and arranging the supply hose connection, the return hose connection, and the power cord connection within the exterior recess of the cold therapy port body.

18. The method of claim 14, wherein:

an interchangeable port body, the interchangeable port body being one of an insulated solid port body, a port having a drain, a port having a vent, and a port having a liquid dispenser;

the interchangeable port body being interchangeable with the cold therapy port body and retainably engageable with the single orifice.

19. The method of claim 18, further comprising the steps of:

incorporating an insulation component configured to provide thermal ins ion into the insulated solid port body.

20. The method of claim 12, wherein:

the circulating pump being a low voltage immersion pump.

* * * * *